(12) United States Patent
Fang et al.

(10) Patent No.: US 11,860,451 B2
(45) Date of Patent: Jan. 2, 2024

(54) CLEANING DEVICE FOR ORTHOKERATOLOGY LENS

(71) Applicant: National Taipei University of Technology, Taipei (TW)

(72) Inventors: Hsu-Wei Fang, Taipei (TW); Chen-Ying Su, Taipei (TW); Hsiao-Hung Chiang, Taipei (TW)

(73) Assignee: National Taipei University of Technology, Taipei (TW)

( * ) Notice: Subject to any disclaimer, the term of this patent is extended or adjusted under 35 U.S.C. 154(b) by 690 days.

(21) Appl. No.: 17/064,189

(22) Filed: Oct. 6, 2020

(65) Prior Publication Data

US 2022/0107516 A1     Apr. 7, 2022

(51) Int. Cl.
  *G02C 13/00*   (2006.01)
  *A61K 9/08*    (2006.01)

(52) U.S. Cl.
  CPC ............. *G02C 13/008* (2013.01); *A61K 9/08* (2013.01)

(58) Field of Classification Search
  CPC ......... G02C 13/008; G02C 13/00; A61L 2/00; A61K 9/08
  See application file for complete search history.

(56) References Cited

U.S. PATENT DOCUMENTS

| | | | | |
|---|---|---|---|---|
| 5,347,674 A * | 9/1994 | Gabbert | ............... | G02C 13/008 15/97.1 |
| 5,456,276 A * | 10/1995 | Shun-Hsien | .......... | A61L 12/086 134/158 |
| 6,183,705 B1 * | 2/2001 | Chang | ................... | G02C 13/008 422/301 |
| 6,193,806 B1 * | 2/2001 | Reed | ..................... | A45C 11/005 134/1 |

\* cited by examiner

*Primary Examiner* — Michael D Jennings
(74) *Attorney, Agent, or Firm* — Birch, Stewart, Kolasch & Birch, LLP

(57) ABSTRACT

Disclosed herein is a cleaning device for orthokeratology lens, comprising a housing, a cap, a gear module, two cleaning shaft, two cleaning head, and a rotating shaft. The housing comprises two orthokeratology lens bases and an opening. The cap is disposed on the opening. The cleaning shaft comprises a first end connecting to the gear module and a second end. The cleaning head is disposed on the second end of the cleaning shaft. The rotating shaft connects to the gear module.

5 Claims, 1 Drawing Sheet

CLEANING DEVICE FOR ORTHOKERATOLOGY LENS

FIELD OF THE INVENTION

The present disclosure is related to a cleaning device for orthokeratology lens; specifically, the device comprises rotatable cleaning head for cleaning lens.

BACKGROUND OF THE INVENTION

Orthokeratology refers to the use of gas-permeable contact lenses that temporarily reshape the cornea to reduce refractive errors such as myopia. This method has gradually directed people's attention since it is more convenient and effective as an alternative choice for eye glass.

Risks of wearing orthokeratology lens are safer than conventional contact lenses, since being worn for much shorter periods in sleep rather than daytime or during working. Orthokeratology lens is also considered generally safer for the youth. However, it is important to maintain good cleaning and hygiene discipline for the user of orthokeratology lens.

Users of contact lens must clean them periodically and preferably should do so when they are taken out and stored for later use. Yet even the most practiced users still take the risks that the lens will be torn or slit by the user's fingernail.

In view of the above, as the cleaning and maintenance of orthokeratology lens is the daily and routine work for a user, there is a need for developing an improved device which, compared to finger scrubbing, reduces the risk of damage or abrasion of the lens and still attain achieve high efficacy of removing residues and cleaning lens, in order to protect the cornea from inflammatory response and contagious germs.

SUMMARY OF THE INVENTION

Disclosed herein is a cleaning device for orthokeratology lens, comprising a housing, a cap, a gear module, two cleaning shaft, two cleaning head, and a rotating shaft. The housing comprises two orthokeratology lens bases and an opening. The cap is disposed on the opening. The cleaning shaft comprises a first end connecting to the gear module and a second end. The cleaning head is disposed on the second end of the cleaning shaft. The rotating shaft connects to the gear module.

In a particular embodiment, the cleaning head is composed of polyurethane.

In a particular embodiment, the cap has a through hole and the rotating shaft is disposed through the through hole.

In a particular embodiment, the orthokeratology lens base has a concave shape.

In a particular embodiment, the housing is used to contain a cleaning buffer for orthokeratology lens.

BRIEF DESCRIPTION OF THE DRAWINGS

The foregoing summary, as well as the following detailed descriptions of the invention, will be better understood when read in conjunction with the appended drawings. In the drawings.

DESCRIPTION OF THE INVENTION

Figure 1:
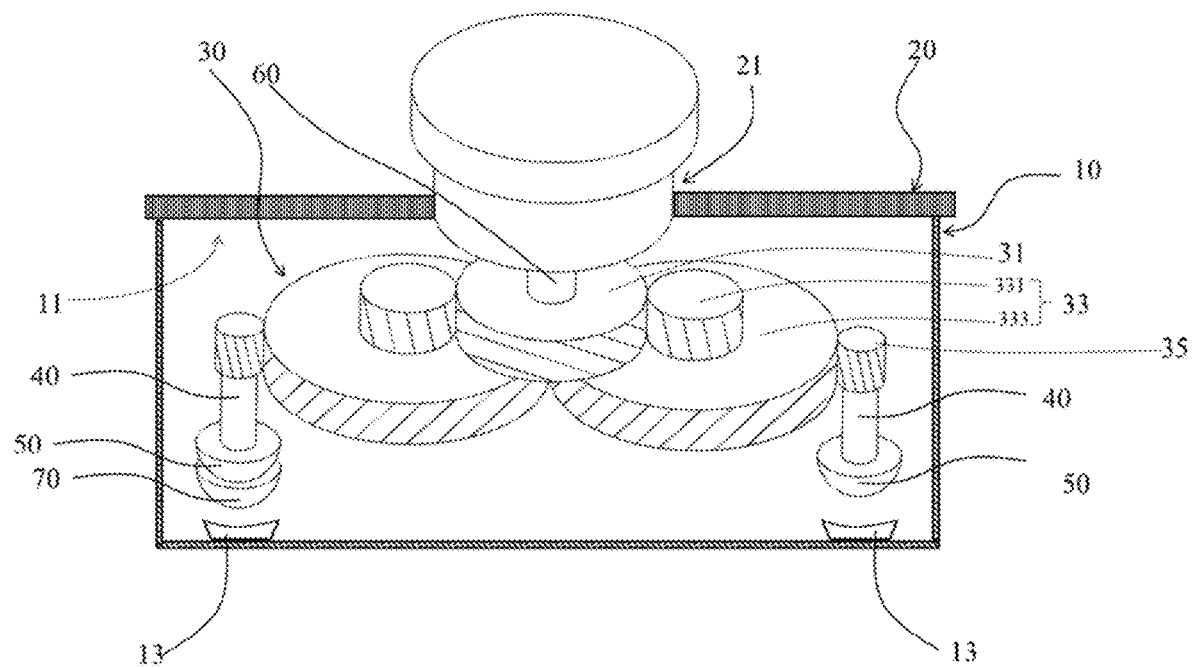
FIG. 1 is a schematic view illustrating the cleaning device for orthokeratology lens as disclosed herein.

The following embodiments when read with the accompanying drawings are made to clearly exhibit the above-mentioned and other technical contents, features and effects of the present disclosure. Through the exposition by means of the specific embodiments, people would further understand the technical means and effects of the present disclosure adopted to achieve the above-indicated objectives. Moreover, as the contents disclosed herein can be readily understood and implemented by a person skilled in the art, all equivalent changes or modifications which do not depart from the concept of the present disclosure shall be encompassed by the appended claims.

Furthermore, the ordinals recited in the specification and the claims such as "first", "second" and so on are intended only to describe the elements claimed and imply or represent neither that the claimed elements have any proceeding ordinals, nor the sequence between one claimed element and another claimed element or between steps of a manufacturing method. The use of these ordinals is merely to differentiate one claimed element having a certain designation from another claimed element having the same designation.

Furthermore, the terms recited in the specifications and the claims such as "above", "over", or "on" are intended not only to directly contact with the other element, but also intended to indirectly contact with the other element.

The present disclosure is related to a cleaning device for orthokeratology lens, comprising: a housing 10, a cap 20, a gear module 30, two cleaning shafts 40, two cleaning heads 50, and a rotating shaft 60.

The housing 10 is used to contain a cleaning buffer for orthokeratology lens 70, and the orthokeratology lens 70 (FIG. 1 only shows one of a pair of lens) is disposed on the bottom of the housing 10 from an opening 11 of the housing 10. Specifically, the housing 10 comprises orthokeratology lens bases 13, which have concave shapes that fit the convex of orthokeratology lens 70. In an alternative embodiment not shown in the figures, the orthokeratology lens bases 13 can be standing supports, such as brackets, and the orthokeratology lens is disposed thereon via a clipping way.

The cap 20 is disposed on the opening 11 of the housing 10, which prevents the buffer from leaking. The cap 20 also comprises a through hole 21, through which the rotating shaft 60 is disposed. In other word, when the cap 20 is covering the housing 10, the rotating shaft 60 would connect the interior space and the external of the housing 10.

The gear module 30 is disposed in the housing 10, which comprises a plurality of gears that is capable to conduct a rotation exerted via the rotating shaft 60. Accordingly, the gear module 30 connects to the rotating shaft 60 and also connects to the cleaning shafts 40.

As described above, the cleaning shafts 40 connect to the gear module 30; the cleaning shafts 40 do not directly connect to the rotating shaft 60 but indirectly connect to the rotating shaft 60 via the gear module 30. The rotating shaft 60, the gear module 30, and the cleaning shafts 40 in combination are configured to exert rotation via the rotating shaft 60 by the user and transfer the force to the cleaning shaft 40. Accordingly, each of the cleaning shaft 40 has a first end and a second end, wherein the first end connects to the gear module 30 and the second end connects to the cleaning head 50.

The cleaning head 50 is disposed on the second end of the cleaning shaft 40 and is used to directly contact with the orthokeratology lens 70. Via the rotation of the cleaning shaft 40, the cleaning head 50 rotates and cleans the orthokeratology lens 70 disposed on the bases 13. In a preferred embodiment, the cleaning head 50 is composed of polymer, for example, polyurethane.

In a specific embodiment, the gear module 30 comprises a first gear 31, two second gears 33, and two third gears 35. The first gear 31 connects to the rotating shaft 60 and can be rotated by the rotating shaft 60. The second gear 33 connects to the first gear 31 and the third gear 35 respectively. The third gear 35 connects to the cleaning shaft 40 and can rotate the cleaning shaft 40.

As the user rotates the rotating shaft 60, the rotation would be exerted to the cleaning shaft 40 according to the configuration of the gear module, and the cleaning head 50 would be rotated by the cleaning shaft 40 such that the orthokeratology lens 70 can be cleaned by the cleaning head 50 via the rotation.

In a more preferred embodiment, the second gear 33 is a double gear including a first part 331 and a second part 333. The diameter of the first part 331 is smaller than the diameter of the second part 333. The first part 333 connects to the first gear 31; the second part 333 connects to the third gear 35.

Example 1

The efficiency of the cleaning device as disclosed herein is tested and compare with the routine method of cleaning by bare hand.

In order to analyze the protein amount affixed on the orthokeratology lens, the orthokeratology lens were immersed in an artificial eyedrops and were cleaned in cleaning buffer (MENICARE PLUS®) by either the device as disclosed herein or by bare hand.

The composition of artificial eyedrop is prepared according to Table 1:

|  | Concentration(mg/mL) |
|---|---|
| Salts | |
| NaCl | 5.26 |
| KCl | 1.19 |
| $Na_2CO_3$ | 1.27 |
| $KHCO_3$ | 0.30 |
| $CaCl_2$ | 0.07 |
| $Na_3C_6H_5O_7$ | 3.41 |
| Urea | 0.072 |
| Glucose | 0.036 |
| HCl | 0.94 |
| Alkyl Carboxylate | 200 μl/L of solution |
| Lipids | |
| Oleic acid | 0.018 |
| Oleic acid methyl ester | 0.012 |
| Triolein | 0.016 |
| Cholesterol | 0.024 |
| Cholesteryl oleate | 0.018 |
| Phosphatidylcholine | 0.0005 |
| Proteins | |
| Lysozyme | 2 |

The orthokeratology lens were immersed in the artificial eyedrops (pH=7.4) as disclosed in Table 1 for 8 hours under 37° C. Then the orthokeratology lens were taken out and cleaned in the immersion of cleaning buffer by the device as disclosed herein or by bare hand. Specifically, the orthokeratology lens were disposed in the device as disclosed herein and the cleaning heads were rotated 20 rounds; on the other hand, other orthokeratology lens were scrubbed by bare hand for 20 times on the convex and concave, respectively. Afterwards, the orthokeratology lens were immersed in the cleaning buffer for 16 hours.

The method of quantitative detection of protein comprises the following steps:

1. Protein reagent A and protein reagent S was mixed in a ratio of 50:1, to obtain a protein reagent A'.
2. The standard lysozyme solution were serially diluted to obtain the solution of lysozyme in different concentrations (0, 0.05, 0.1, 0.2, 0.4, 0.8, 1.6, 3.2 mg/ml).
3. 100 μl standard lysozyme solution or the solution used to clean and immerse orthokeratology lens was added in 15 ml centrifugation tube and 500 μl Protein Reagent A' was further added followed by 10 seconds vortexing. The mixture was mixed thoroughly.
4. After the solution was mixed, 4,000 μl Protein Reagent B was added followed by 10 seconds vortexing. The mixture was left for reaction for 15 minutes.
5. The absorbance was detected by an ELISA reader (wavelength: 750 nm, detection completed in one hour).

Figure 2:
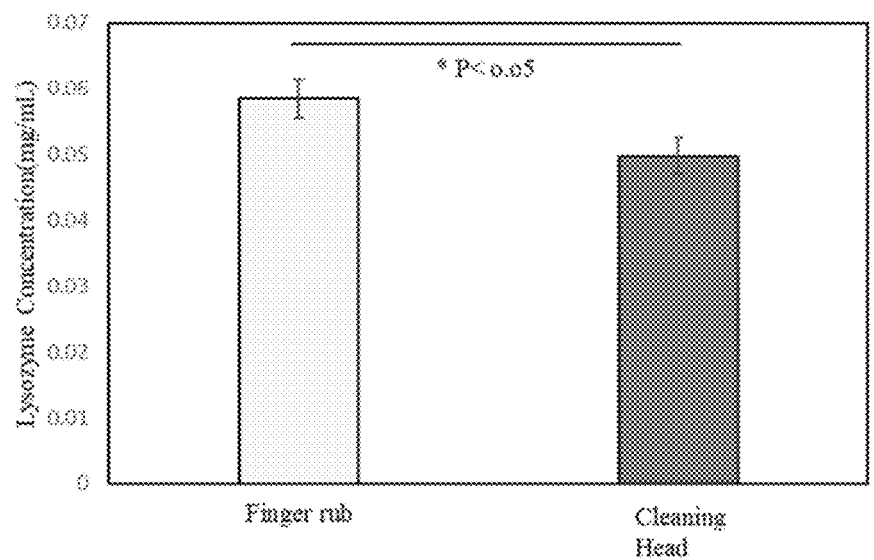
FIG. 2 is a graphic illustrating the comparison of the cleaning efficiency of conventional finger scrubbing and the device as disclosed herein; t test: $p<0.05$.

The result of detection of absorbance is disclosed in FIG. 2. The result shows that after cleaning, the average lysozyme concentration in the solution derived from the group in which the orthokeratology lens were scrubbed by bare hand, was 0.0584 mg/ml; whereas the lysozyme concentration from the group cleaned by the device as disclosed herein, was 0.049 mg/ml.

The result was analyzed via statistic approach. The analysis result via t test shows that the p value among the experiment groups is less than 0.05, which implies the significance of improvement of the device as disclosed herein compared to conventional method (scrubbing by bare hand).

Although the present disclosure is disclosed above by preferred embodiments, the preferred embodiments are not restrictive of the present disclosure. Changes and modifications made by persons skilled in the art to the preferred embodiments without departing from the spirit of the present disclosure must be deemed falling within the scope of the present disclosure. Accordingly, the legal protection for the present disclosure should be defined by the appended claims.

We claim:

1. A cleaning device for orthokeratology lens, comprising a housing, comprising two orthokeratology lens bases and an opening;
a cap, disposed on the opening;
a gear module;
at least one cleaning shaft, comprising a first end connecting to the gear module and a second end;
at least one cleaning head, disposed on the second end of the at least one cleaning shaft; and
a rotating shaft, connecting to the gear module.

2. The device according to claim 1, wherein the at least one cleaning head is composed of polyurethane.

3. The device according to claim 1, wherein the cap has a through hole and the rotating shaft is disposed through the through hole.

4. The device according to claim 1, wherein the orthokeratology lens base has a concave shape.

5. The device according to claim 1, wherein the housing is used to contain a cleaning buffer for orthokeratology lens.

* * * * *